United States Patent
Yasuda

(10) Patent No.: US 8,557,986 B2
(45) Date of Patent: Oct. 15, 2013

(54) METHOD OF PRODUCING POLYSACCHARIDE DERIVATIVES

(75) Inventor: Yousuke Yasuda, Higashiyamato (JP)

(73) Assignee: Seikagaku Corporation, Tokyo (JP)

( * ) Notice: Subject to any disclaimer, the term of this patent is extended or adjusted under 35 U.S.C. 154(b) by 758 days.

(21) Appl. No.: 12/299,091

(22) PCT Filed: Apr. 27, 2007

(86) PCT No.: PCT/JP2007/059555
§ 371 (c)(1),
(2), (4) Date: Nov. 6, 2008

(87) PCT Pub. No.: WO2007/126154
PCT Pub. Date: Nov. 8, 2007

(65) Prior Publication Data
US 2009/0104678 A1    Apr. 23, 2009

(30) Foreign Application Priority Data
May 1, 2006  (JP) ................................. 2006-127837

(51) Int. Cl.
C07D 251/46    (2006.01)

(52) U.S. Cl.
CPC .................................. *C07D 251/46* (2013.01)
USPC ...................................................... 544/194

(58) Field of Classification Search
None
See application file for complete search history.

(56) References Cited

U.S. PATENT DOCUMENTS

| | | | | |
|---|---|---|---|---|
| 6,031,017 A | * | 2/2000 | Waki et al. ....................... | 522/84 |
| 6,458,948 B1 | | 10/2002 | Iwasaki | |
| 7,462,715 B2 | * | 12/2008 | Kunishima .................... | 544/219 |
| 7,879,817 B2 | * | 2/2011 | Miyamoto et al. .............. | 514/54 |
| 2005/0118199 A1 | * | 6/2005 | Esser et al. ................. | 424/244.1 |
| 2007/0197465 A1 | | 8/2007 | Ikeya et al. | |

FOREIGN PATENT DOCUMENTS

| | | | |
|---|---|---|---|
| CN | 1245812 A | | 3/2000 |
| EP | 1 082 963 | | 3/2001 |
| EP | 1 085 000 | | 10/2004 |
| EP | 1 710 257 | | 10/2006 |
| JP | 2004-018750 | | 1/2004 |
| JP | 2005-281372 | | 10/2005 |
| WO | WO 00/53544 | | 9/2000 |
| WO | WO 2004/085487 | | 10/2004 |
| WO | WO 2005/066214 | | 7/2005 |
| WO | WO 2005/085294 | | 9/2005 |
| WO | WO2005/095464 | * | 10/2005 |

OTHER PUBLICATIONS

Text of First Office Action issued Sep. 17, 2010 to corresponding Chinese patent application No. 200780015807.0.
Farkas, et al. "Efficient Activation of Carboxyl Polysaccharides for the Preparation of Conjugates," *Carbohydrate Polymers*, vol. 68, No. 1, pp. 187-190, Feb. 7, 2007.
Kunishima, et al. "Formation of Carboxamides by Direct Condensation of Carboxylic Acids and Amines in Alcohols using a New Alcohol- and Water-Soluble Condensing Agent: DMT-MM," *Tetrahedron*, vol. 57, No. 8, pp. 1551-1558, Feb. 18, 2001.
Kunishima, et al. "4-(4,6-Dimethoxy-1,3,5-triazin-2-yl)-4-methylmorpholinium Chloride: An Efficient Condensing Agent Leading to the Formation of Amides and Esters," *Tetrahedron*, vol. 55, No. 46, pp. 13159-13170, Nov. 12, 1999.
International Search Report dated Jul. 11, 2007.
Second Office Action issued on May 11, 2011 by SIPO to the corresponding Chinese patent application No. 200780015807.0.
Decision on Rejection issued on Jan. 10, 2012 by SIPO to the corresponding Chinese patent application No. 200780015807.0.

* cited by examiner

*Primary Examiner* — Eric S Olson
(74) *Attorney, Agent, or Firm* — Knobbe, Martens, Olson & Bear LLP

(57) ABSTRACT

A polysaccharide derivative having a high solubility in an aqueous solvent is produced. The production method of the present invention uses a compound shown by the general formula (1) as a condensing agent and allows a polysaccharide having a carboxyl group to react with an an organic compound having a functional group capable of condensing with the carboxyl group to prepare the polysaccharide derivative:

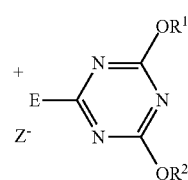

(1)

$R^1$ and $R^2$ independently represent a substituent selected among alkyl groups of 1 to 4 carbon atoms and aryl groups of 6 to 8 carbon atoms; $Z^-$ represents a counter anion; and $E^+$ represents an organic group shown as:

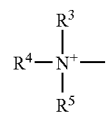

$R^3$, $R^4$, and $R^5$ independently represent an organic group having at least one carbon atom directly bound to a quaternary nitrogen atom and any two or all of $R^3$, $R^4$, and $R^5$ may link together to form a cyclic structure.

20 Claims, No Drawings

METHOD OF PRODUCING POLYSACCHARIDE DERIVATIVES

CROSS-REFERENCE TO RELATED APPLICATIONS

This application is the U.S. National Phase under 35 U.S.C. §371 of International Application PCT/JP2007/059555, filed Apr. 27, 2007, which claims priority to JP 2006-127837, filed May 1, 2006.

TECHNICAL FIELD

The present invention relates to a method of producing polysaccharide derivatives.

BACKGROUND ART

There are diverse polysaccharides according to the types of their constituent monosaccharides. The polysaccharides have various molecular weights, properties, and physiological functions and are the popular target of intensive researches.

As is known in the art, coupling of a compound having a functional group capable of condensing with a carboxyl group with that of hyaluronic acid, which is known as a high-molecular weight polysaccharide, decreases the hydrophilicity of the resulting hyaluronic acid derivative and causes the problem of sparse solubility or even insolubility.

One conventionally known technique for coupling carboxyl-linkable, nucleophilic functional group and carboxyl group of hyaluronic acid uses water-soluble carbodiimide (WSC) to allow hyaluronic acid to react with amino group in aqueous solvent (JP 2004-018750 and WO2005/085294). This technique is hereafter referred to as the WSC method. The hyaluronic acid derivative obtained by the WSC method has the problem of sparse solubility or insolubility. According to the description in JP 2004-018750, when the rate of the introduced compound per disaccharide unit of hyaluronic acid (degree of substitution) is not less than 0.05%, the isolated hyaluronic acid derivative may be insoluble in neutral aqueous solvents. When the degree of substitution is not less than 5%, the isolated hyaluronic acid derivative is insoluble in aqueous solvents.

For this insolubility problem, the production method proposed in JP 2004-018750 adds a base to the reaction solution after the condensation reaction of hyaluronic acid. This alkaline treatment allows the compound by the WSC method to be able to dissolve in neutral aqueous solvent. WO2005/085294 also adopts this alkaline treatment step of JP 2004-018750 to prepare a neutral aqueous solution of the resulting hyaluronic acid derivative. Namely, JP 2004-018750 and WO2005/085294 adopt the two-step preparation process including the condensation reaction step by the WSC method and the alkaline treatment step to prepare a hyaluronic acid derivative that is soluble in an aqueous solvent.

As described in JP 2004-018750, the hyaluronic acid derivative prepared by the conventional WSC method is expected to have a change in its higher-order structure, which can be observed as the phenomenon of insolubility in the neutral aqueous solvent. Condensation condition of the WSC method causes the hyaluronic acid derivative to be insoluble in the neutral aqueous solution. The alkaline treatment after the WSC method as described in JP 2004-018750 recovers the solubility of the hyaluronic acid derivative. The recovery of the water solubility is ascribed to a further change or restoration of the higher-order structure which has been changed by the WSC method.

The base-adding step (alkaline treatment) described in JP 2004-018750 further changes or restores the higher-order structure which has been changed in the course of the condensation reaction to regain the once-lost high affinity to the aqueous solvent.

A commercially available condensing agent 4-(4,6-dimethoxy-1,3,5-triazin-2-yl)-4-methylmorpholinium chloride (DMT-MM) works for condensation of a carboxyl group and a carboxyl-linkable, nucleophilic functional group and is mainly used for synthesis of amide compounds by condensation of low-molecular substances. According to Tetrahedron 55 (1999) 13159, DMT-MM activates a carboxyl group in aqueous solvent and helps to form an amide bond with an amino group at a high rate. JP 2005-281372 describes application of DMT-MM for forming an amide bond between a carboxyl group of a carboxyl group-introduced cyclodextrin derivative and an amino group of chitosan. This production method of JP 2005-281372, however, aims to give an insoluble derivative. There has been no report regarding application of DMT-MM for the condensation reaction of a carboxyl group of a high molecular weight polysaccharide (for example, hyaluronic acid) with a carboxyl-linkable, functional group of an organic compound with a view to preparing a water-soluble derivative. There has also been no report describing the properties of an aqueous solution of the resulting derivative or the change of the higher-order structure of the resulting derivative.

DISCLOSURE OF THE INVENTION

Conventionally for the condensation reaction, water-soluble condensing agent (water-soluble carbodiimide) has been used to form a chemical bond between a carboxyl group of a polysaccharide and a functional group of an organic compound that can condense with the carboxyl group. The prepared polysaccharide derivative is, however, not homogeneously soluble in a neutral aqueous solvent. To increase the solubility of the product, an extra step of adding a base to the reaction solution is required after the condensation reaction.

There are high demand of developing a simple procedure which enable to produce a highly soluble product by the coupling reaction of a polysaccharide having a carboxyl group and an organic compound having a functional group capable of condensing with the carboxyl group.

As mentioned above, the prior art polysaccharide derivatives prepared by the reaction of hyaluronic acid or another polysaccharide having a carboxyl group and an organic compound having a functional group capable of condensing with the carboxyl group have significant changes in their higher order structures and are not easily soluble in neutral aqueous solvents.

The inventors have made intensive studies to solve this problem of the prior art and to devise a simple and efficient production method of polysaccharide derivatives. As the result of the intensive studies, the inventors have found that the use of a specific condensing agent, in place of the conventionally used condensing agent WSC, readily and efficiently yields useful polysaccharide derivatives that have good solubility in aqueous solvents, and thereby completed the present invention.

The present invention is thus directed to a simple and efficient method of producing high molecular weight polysaccharide derivatives.

It is an object of the present invention to provide a method of producing a polysaccharide derivative comprising a polysaccharide having a carboxyl group bound to an organic compound having a functional group capable of condensing with the carboxyl group, which comprises allowing the polysaccharide to react with the organic compound by the use of a condensing agent shown by the general formula (1):

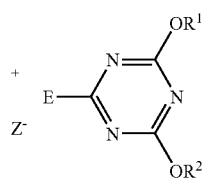

(1)

R¹ and R² independently represent a substituent selected among alkyl groups of 1 to 4 carbon atoms and aryl groups of 6 to 8 carbon atoms; $Z^-$ represents a counter anion; and $E^+$ represents the following group:

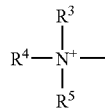

$R^3$, $R^4$, and $R^5$ independently represent an organic group having at least one carbon atom directly bound to the quaternary nitrogen atom and any two or all of $R^3$, $R^4$, and $R^5$ may link together to form a cyclic structure.

It is a further object of the present invention to provide the method as described above, wherein the polysaccharide having a carboxyl group has a molecular weight of not less than 10,000.

It is a further object of the present invention to provide the method as described above, wherein the polysaccharide having a carboxyl group is glycosaminoglycan.

It is a further object of the present invention to provide the method as described above, wherein the polysaccharide having a carboxyl group is hyaluronic acid.

It is a further object of the present invention to provide the method as described above, wherein the hyaluronic acid has a weight average molecular weight of not less than 100,000.

It is a further object of the present invention to provide the method as described above, wherein the organic compound having a functional group capable of condensing with a carboxyl group is an organic compound having a hydroxyl group or an amino group, and wherein the polysaccharide and the organic compound are bound by ester bond or amide bond.

It is a further object of the present invention to provide the method as described above, wherein the organic compound having a functional group capable of condensing with a carboxyl group is a compound having at least one amino group, and wherein the polysaccharide and the organic compound are bound by amide bond.

It is a further object of the present invention to provide the method as described above, wherein the organic compound having a functional group capable of condensing with the carboxyl group is a compound that is prepared by covalently binding a spacer substance having at least two functional groups to a physiologically active substance having a functional group or to a medicinal substance having a functional group, and the at least two functional groups of the spacer substance include a functional group capable of condensing with a carboxyl group and a functional group capable of forming a covalent bond with the functional group of the physiologically active substance or the medicinal substance.

It is a further object of the present invention to provide the method as described above, wherein the medicinal substance is a nonsteroidal anti-inflammatory drug or a disease-modifying antirheumatic drug.

It is a further object of the present invention to provide the method as described above, wherein the covalent bond is ester bond or amide bond.

It is a further object of the present invention to provide the method as described above, wherein the spacer substance having the at least two functional groups is selected among a group consisting of aminoalcohols, alkylenediamines, and amino acids.

It is a further object of the present invention to provide the method as described above, wherein in the general formula (1), R¹ and R² are independently selected from the group of a methyl group, an ethyl group, and a phenyl group, $E^+$ is an N-methylmorpholinium group, and $Z^-$ is a chlorine anion, a perchlorate anion, or a tetrafluoroborate anion.

It is a further object of the present invention to provide the method as described above, wherein the compound shown by the general formula (1) is 4-(4,6-dimethoxy-1,3,5-triazin-2-yl)-4-methylmorpholinium chloride.

It is a further object of the present invention to provide a method of producing a polysaccharide derivative, comprising:

(A) producing a polysaccharide derivative by the method as described above; and (B) allowing a base to react with the polysaccharide derivative produced in the step (A).

It is a further object of the present invention to provide the method as described above, wherein 1% (w/v) aqueous solution of the polysaccharide derivative is not cloudy but is clear and contains no visible solid substance at the condition where the polysaccharide derivative is dissolved in water by shaking at 220 rpm overnight at room temperature.

It is a further object of the present invention to provide the method as described above, wherein the 1% (w/v) aqueous solution has no significant decrease in concentration after filtration through a porous filter of 0.22 μm in pore diameter.

It is a further object of the present invention to provide a method of producing a hyaluronic acid derivative comprising a hyaluronic acid bound to a nonsteroidal anti-inflammatory drug, carboxylic group of which is esterified with a hydroxyl group of an aminoalcohol, which comprises allowing an amino group of aminoalcohol of the esterified nonsteroidal anti-inflammatory drug to condense with a carboxyl group of hyaluronic acid, wherein the condensation reaction is conducted by the use of a condensing agent shown by the general formula (1), and wherein the nonsteroidal anti-inflammatory drug has a structure shown by the general formula (3):

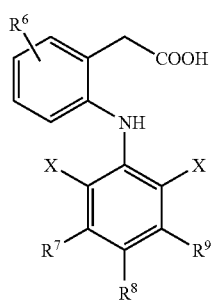

(3)

$R^6$ represents a hydrogen atom or a substituent selected among lower alkyl groups and lower alkoxyl groups; $R^7$, $R^8$, and $R^9$ independently represent a halogen atom, a hydrogen atom, or a substituent selected among lower alkyl groups, lower alkoxyl groups, and hydroxyl group; and X independently represents a halogen atom or a substituent selected among lower alkyl groups and trifluoromethyl group, and at least one of X is a halogen atom.

It is a further object of the present invention to provide the method as described above, wherein the compound shown in the general formula (1) is 4-(4,6-dimethoxy-1,3,5-triazin-2-yl)-4-methylmorpholinium chloride.

It is a further object of the present invention to provide the method as described above, wherein the aminoalcohol is shown by the following formula:

n represents an integer of 2 to 12.

DESCRIPTION THE PREFERRED EMBODIMENTS

The present invention is described below in detail with reference to some embodiments.

Unless otherwise specified, an aqueous solvent to be used in the present invention may be any of water, water-containing buffer solutions, aqueous solutions and buffer solutions containing pharmaceutically acceptable metal salts and pH adjusters. Typical examples of the aqueous solvent include distilled water for injection, phosphate buffered saline, and normal saline solution. Unless otherwise specified, the molecular weight of the polysaccharide is expressed by the weight average molecular weight in the present invention.

The present invention provides a novel method of producing polysaccharide derivatives.

The polysaccharide to be used as a starting material in the method of the present invention is a polysaccharide having a carboxyl group and is preferably a polysaccharide having a carboxyl group and a molecular weight of not less than 10,000. The polysaccharide may be any of natural polysaccharides which are extracted and isolated from, for example, animals, artificial polysaccharides which are produced by genetically modified microorganisms, and synthetic polysaccharides which are produced by chemical syntheses, as well as commercially available polysaccharides. The polysaccharide may be a glycosaminoglycan composed of monosaccharide having a carboxyl group. The polysaccharide may also be a chemically carboxymethylated derivative of a neutral carbohydrate polymer, such as carboxymethylcellulose. Specific examples of glycosaminoglycan having a carboxyl group include sodium hyaluronate, chondroitin, chondroitin sulfate, heparin, heparan sulfate, and N-acetylheparosan.

The effect of the production method of the invention, which is described later in detail, the high solubility of the resulting polysaccharide derivative in an aqueous solvent, is especially prominent in a polysaccharide having a high molecular weight and a relatively low content of such substituent as sulfate group that enhances the aqueous solubility of the polysaccharide. A typical example of the polysaccharide profiting the significant effect is hyaluronic acid.

The hyaluronic acid is a polymer having a disaccharide unit of D-glucoronic acid and N-acetyl-D-glucosamine. In the present description, the hyaluronic acid may be a modified hyaluronic acid having a repeated structure of the disaccharide unit and at least one unmodified carboxyl group. The modified hyaluronic acid to be used as the starting material in the production method of the invention is any modified hyaluronic acid that is derived from hyaluronic acid and has at least one unmodified carboxyl group. One typical example is a modified hyaluronic acid having another low-molecular compound (for example, an alcohol, a medicinal substance, or cinnamate derivatives) that is introduced into part of the carboxyl group of the hyaluronic acid.

The hyaluronic acid to be used as the starting material may be any of various pharmaceutically acceptable salts of hyaluronic acid and modified hyaluronic acid.

The pharmaceutically acceptable salts include alkali metal salts such as sodium salt and potassium salt and alkaline earth metal salts such as magnesium salt and calcium salt. The alkali metal salts are preferable, and the sodium salt is particularly preferable.

The weight average molecular weight of the hyaluronic acid to be used as the starting material is not particularly limited but is preferably in a range of 10,000 to 10,000,000, which shows characteristic of a polysaccharide polymer. The weight average molecular weight of the hyaluronic acid is more preferably in a range of 100,000 to 5,000,000 or further more preferably in a range of 500,000 to 3,000,000.

The organic compound having a functional group capable of condensing with a carboxyl group may be compound that donates or shares an electron to or with an atom of a low electron density and accordingly is able to condense with a carboxyl group. The functional group may be a hydroxyl group or an amino group. The organic compound having a functional group capable of condensing with a carboxyl group is preferably a compound having at least one amino group. The polysaccharide having a carboxyl group and the organic compound having the functional group capable of condensing with the carboxyl group are preferably linked to each other by ester bond or amide bond. Especially preferable is the amide bond, which ensures high yields of stable products by reactions in water-containing solvents.

The organic compound having a functional group capable of condensing with a carboxyl group is appropriately selected among various organic compounds having functional groups that are able to condense with a carboxyl group according to the purpose and the application of the resulting polysaccharide derivatives.

Typical examples of the organic compound having a functional group capable of condensing with a carboxyl group include low molecular weight compounds of linear alkylamines, amino acids, and aminoalcohols and their derivatives. The aminoalcohol may be shown by the formula of:

n represents an integer of 2 to 12.

In the case of preparation of the polysaccharide derivative by condensation of a medicinal substance or a physiologically active substance and the polysaccharide having a carboxyl group, the organic compound having a functional group capable of condensing with a carboxyl group is appropriately selected according to a desired pharmaceutical effect or a desired physiological activity and the application of the resulting polysaccharide derivative. Available examples for this purpose include various medicinal substances described below, as well as cytokines, hormones, growth factors, enzymes, and other diverse physiologically active substances.

Typical examples of the medicinal substance include non-steroidal anti-inflammatory drugs (NSAIDs) and disease-modifying antirheumatic drugs (DMARDs) having a functional group, such a carboxyl group, hydroxyl group, or amino group, in their chemical structures.

There are diversity of NSAIDs including salicylate NSAIDs, fenamate NSAIDs, arylacetic acid NSAIDs, propionic acid NSAIDs, and oxicam NSAIDs, as well as tiaramide, tolmetin, diflunisal, acetaminophen, floctafenine, and tinoridine. Compounds having a structure shown by the formula (2) are preferably used as the medicinal substance:

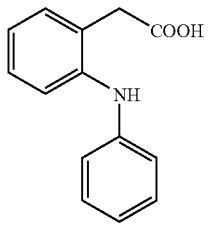

(2)

Especially preferable are compounds shown by the general formula (3):

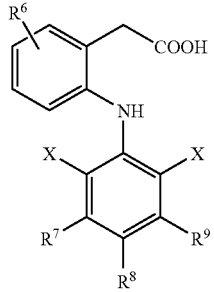

(3)

In the general formula (3), $R^6$ represents a hydrogen atom or a substituent selected among lower alkyl groups and lower alkoxyl groups.

$R^7$, $R^8$, and $R^9$ independently represent a halogen atom, a hydrogen atom, or a substituent selected among lower alkyl groups, lower alkoxyl groups, and hydroxyl group.

X independently represents a halogen atom or a substituent selected among lower alkyl groups and trifluoromethyl group, and at least one of X is a halogen atom.

Among the lower alkyl groups and the lower alkoxyl groups, linear or branched lower alkyl groups and lower alkoxyl groups, either of which has 1 to 12 carbon atoms, are preferable, and linear or branched lower alkyl groups and lower alkoxyl groups, either of which has 1 to 6 carbon atoms, are particularly preferable.

$R^6$ is preferably bound at position 5 of the benzene ring that has a carboxymethyl group at position 1 and an amino residue at position 2.

The compound shown by the general formula (3) includes, for example, a compound disclosed in WO99/11605, the disclosure of which is hereby incorporated by reference in its entirety.

Compounds shown by the general formula (4) are also preferable:

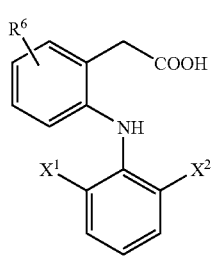

(4)

In the general formula (4), $R^{10}$ represents a hydrogen atom or a substituent selected among lower alkyl groups and lower alkoxyl groups. $R^{10}$ is preferably a hydrogen atom or a substituent selected among linear or branched lower alkyl groups having 1 to 12 carbon atoms, and is more specifically a hydrogen atom or a substituent selected among lower alkyl groups having 1 to 4 carbon atoms.

$X^1$ and $X^2$ independently represents a halogen atom or a substituent selected among lower alkyl groups and trifluoromethyl group, and at least one of $X^1$ and $X^2$ is a halogen atom. Both of $X^1$ and $X^2$ are preferably a halogen atom and are more preferably either a fluorine atom or a chlorine atom.

One typical example of the compound shown by the general formula (4) is diclofenac having a hydrogen atom for $R^{10}$ and chlorine atoms for both $X^1$ and $X^2$.

The organic compound having a functional group capable of condensing with a carboxyl group may be a physiologically active substance or medicinal substance originally having the functional group. The organic compound may otherwise have a functional group that is introduced for the condensation reaction with the polysaccharide. In the latter case, the organic compound having the functional group capable of condensing with a carboxyl group may be obtained by covalently linking a physiologically active substance or a medicinal substance to a spacer substance having at least two functional groups, or by covalently linking a photoreactive compound, such as cinnamic acid or a cinnamate derivative, to a spacer substance having at least two functional groups.

The spacer substance having at least two functional groups has at least one first functional group capable of condensing with a carboxyl group such as amino group and hydroxyl group and a second functional group capable of condensing with a functional group of the physiologically active substance or the medicinal substance, and accordingly the second functional group of the spacer substance condenses with the functional group of the physiologically active substance or the medicinal substance by covalent bond to prepare an organic compound having a functional group (the first functional group) capable of condensing with a carboxyl group.

For example, the spacer substance having at least two functional groups is linked with the physiologically active substance or the chemical substance having the functional group by ester bond or amide bond.

Even when the physiologically active substance or the medicinal substance originally has no functional group capable of condensing with a carboxyl group, the covalently linking of the second functional group of the spacer substance to the functional group of the physiologically active substance or the medicinal substance yields a physiologically active substance or the medicinal substance having the functional group (the first functional group) capable of condensing with a carboxyl group.

The spacer substance having at least two functional groups is appropriately selected according to the purpose and the application of the resulting polysaccharide derivative to be obtained by the production method of the invention.

The spacer substance having at least two functional groups may be selected corresponding to the functional group of the NSAID described above to form a covalent compound.

The first functional group of the spacer substance is a functional group capable of condensing with a carboxyl group of the polysaccharide. A spacer substance having a carboxyl group as the second functional group is applicable to be linked to a hydroxyl group of the NSAID or the DMARD by ester bond. A spacer substance having a hydroxyl group as the second functional group or a spacer substance having an amino group as the second functional group is applicable to be linked to the carboxyl group of the NSAID or the DMARD by ester bond or by amide bond, respectively. The bond of the spacer substance with the medicinal substance is appropriately selected according to the purpose and the application of the final product to be obtained by the production method of the invention. The ester bond is preferably selected for the easy decomposition of the resulting compound in a living body.

Available examples of the spacer compound having at least two functional groups to be linked to the NSAID or the DMARD mentioned above include aminoalcohols shown by the formula of $H_2N$—$(CH_2)_n$—OH (n represents an integer of 2 to 18 or more preferably an integer of 2 to 12), alkylenediamines, and aminocarboxylic acids. Preferable examples are diaminoalkanes having 2 to 18 carbon atoms, substituted or non-substituted aminoalkyl alcohols having 2 to 12 carbon atoms, and amino acids. Specific examples thereof include glycine, β-alanine, γ-aminobutyric acid, and substituted and non-substituted linear or branched aminoalkyl alcohols having 2 to 5 carbon atoms.

The aminoalcohol may also be used as the spacer substance to be linked to the photoreactive compound, such as cinnamic acid or cinnamate derivative.

The condensing agent used in the production method of the present invention is a compound shown by the general formula (1):

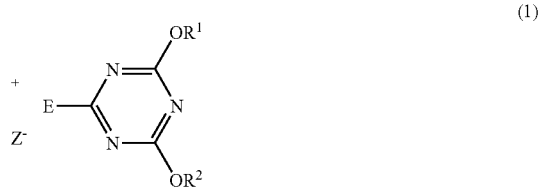

$R^1$ and $R^2$ independently represent a substituent selected among alkyl groups of 1 to 4 carbon atoms and aryl groups of 6 to 8 carbon atoms; $Z^-$ represents a counter anion; and $E^+$ represents an organic group shown as:

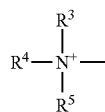

$R^3$, $R^4$, and $R^5$ independently represent an organic group having at least one carbon atom directly bound to a quaternary nitrogen atom and any two or all of $R^3$, $R^4$, and $R^5$ may link together to form a cyclic structure.

In the compound shown by the general formula (1), it is preferable that each of $R^1$ and $R^2$ represents a methyl group, an ethyl group, or a phenyl group, $E^+$ represents an N-methylmorpholinium group, and $Z^-$ represents a chlorine anion, a perchlorate anion, or a tetrafluoroborate anion.

The compound shown by the general formula (1) is, for example, a quaternary ammonium salt disclosed in WO00/53544, the disclosure of which is hereby incorporated by reference in its entirety.

A specific example of the compound shown by the general formula (1) is 4-(4,6-dimethoxy-1,3,5-triazin-2-yl)-4-methylmorpholinium chloride, in which both of $R^1$ and $R^2$ are methyl groups, $E^+$ is an N-methylmorpholinium group, and $Z^-$ is a chlorine anion.

In the production method of the present invention, the condensing agent to be used for the condensation reaction is not necessarily an isolated substance, but may be formed in the condensation reaction system. Namely, the condensing agent to be used in the production method of the invention may be a substance (reaction material) that forms the compound shown by the general formula (1) in the condensation reaction system.

The reaction conditions in the production method of the invention are described below, although they can be appropriately selected by one skilled in the art to obtain desired polysaccharide derivatives.

The amount of the condensing agent to be used for the condensation reaction is preferably in a range of 0.0005 to 0.4 equivalents, more preferably in a range of 0.001 to 0.3 equivalents, or further more preferably in a range of 0.003 to 0.25 equivalents with respect to one mole of the carboxyl group of the polysaccharide as the starting material. When the purity of the condensing agent is unknown, for example, because of the presence of hydrated water, the purity of the condensing agent is calculated as the factor of condensation activity from the condensation yield of a low molecular weight carboxylic acid and a low molecular weight amine, and the calculated purity is used for estimation of the molar number of the condensing agent per unit weight.

The amount of the organic compound having a functional group capable of condensing with a carboxyl group is not particularly limited as long as the amount is not less than the amount of the condensing agent to be used. When the organic compound links to the polysaccharide by means of amide bond, the molar quantity of the organic compound is preferably equal to the molar quantity of the condensing agent for the better purification efficiency.

The reaction temperature is in a range of 0° C. to 60° C., preferably in a range of 4° C. to 50° C., and more preferably in a range of 15° C. to 40° C.

The reaction time depends upon the reaction temperature and the reactivity of the functional group capable of condensing with a carboxyl group. The reaction time is not particularly limited but may be, for example, 3 to 24 hours.

Available examples of the solvent for the reaction solution include water, water-miscible organic solvents, and solvent mixtures thereof. Ethanol is used as a preferable water-miscible organic solvent, because of its low toxicity to human bodies and its applicability against various regulations. The solvents and their mixing ratio are appropriately determined according to the solubility of the polysaccharide having a carboxyl group, such as hyaluronic acid, the reaction efficiency, and the purification efficiency. In some cases, the organic solvents may not be used for the reaction solution.

The conventional WSC method generally uses 1,4-dixoane and tetrahydrofuran as the organic solvents for the reaction solution. The production method of the present invention does not use such toxic organic solvents and thus reduces the toxicity of the solvent of the reaction solution.

The polysaccharide derivative prepared by the production method of the present invention may be purified by any of conventionally known techniques that can be applied for purification of polysaccharides. The organic solvent precipitation method using ethanol and the gel filtration column chromatography are preferably applied for the purification.

The polysaccharide derivative obtained by the production method of the present invention has high solubility in neutral aqueous solvents.

The hyaluronic acid derivative produced by the production method of the present invention is compared with the hyaluronic acid derivative produced by the conventional WSC method. These hyaluronic acid derivatives have similar chemical structures by condensation of hyaluronic acid having a carboxyl group and the organic compound having a functional group capable of condensing with a carboxyl group, but have significantly different solubilities in water. This fact suggests the remarkable difference in the higher-order structures of these hyaluronic acid derivatives. Under the condition of an identical degree of substitution of organic compound, the hyaluronic acid derivative prepared by the production method of the present invention is highly soluble in an aqueous solvent and yields a clear and viscous solution without any visible solid substance, while the hyaluronic acid derivative prepared by the conventional WSC method is not soluble in distilled water and yields a suspension of insoluble matters. Such difference between the hyaluronic acid derivative by the production method of the present invention and the hyaluronic acid derivative by the WSC method is found at least in hyaluronic acid derivatives having the degree of substitution of the organic compound in the range of 5% to 20%, although the difference may be affected by the hydrophobicity of the introduced organic compound.

JP2004-18750 discloses the extra step of adding a base to the reaction solution, in addition to the production process of the hyaluronic acid derivative by the conventional WSC method. According to this document, the resulting hyaluronic acid derivative has a high molecular dispersion in water. However, the molecular dispersion of this hyaluronic acid derivative in water is once lowered in the course of or after the condensation reaction by the WSC method. The lowered molecular dispersion suggests a change in higher-order structure of the resulting hyaluronic acid derivative. Addition of the base may recover the once-lowered molecular dispersion. But this does not mean that the resulting hyaluronic acid derivative recovers its original higher-order structure of the hyaluronic acid.

The production method of the present invention, on the other hand, yields the hyaluronic acid derivative without damaging the original higher-order structure of the hyaluronic acid.

The prior art technique disclosed in JP2004-18750 essentially requires the extra step of adding a base to change or restore the higher-order structure of hyaluronic acid and recover the once-lowered solubility of the hyaluronic acid derivative in the aqueous solvent. Careful selection of an appropriate alkaline treatment condition is thus required for preventing alteration of the hyaluronic acid derivative under basic conditions. The use of an adequate amount of a weak inorganic base is recommended in the method of JP2004-18750. The production method of the present invention, on the other hand, does not require such careful selection of the reaction conditions for the purpose of preventing alteration of the hyaluronic acid derivative, as long as the above-mentioned reaction conditions.

In the production method of the present invention, an extra step of adding a base to the reaction solution as disclosed in JP2004-18750 may also be performed after the condensation reaction in order to impart higher water solubility to the resulting polysaccharide derivative. In the base-adding extra step, an aqueous sodium hydrogen carbonate solution may be added to the reaction solution of the polysaccharide derivative. Instead of sodium hydrogen carbonate, any other suitable base disclosed in JP2004-18750 may also be used. For example, an inorganic base, sodium carbonate, may be used to make the reaction solution mildly alkaline.

The hyaluronic acid derivative and the other polysaccharide derivatives produced by the method of the present invention have preferably the characteristics as described below.

The permeability through a porous filter is a typical index of the molecular dispersion or the solubility of the polysaccharide derivative in water. For example, a 1.0% (w/v) neutral aqueous solution of the resulting hyaluronic acid derivative is prepared and is passed through a porous filter. The concentration of the aqueous hyaluronic acid derivative solution is measured before and after the filtration. Little or no decrease in the concentration of the hyaluronic acid derivative indicates the high water solubility of the hyaluronic acid derivative. The polysaccharide derivative obtained by the production method of the present invention is neither adsorbed nor removed by filtration of its 1.0% (w/v) aqueous solution through a porous filter (having a pore diameter of 5 µm or 0.45 µm) and has no significant change in concentration before and after the filtration. As described later in Examples, when the degree of substitution of the organic compound is not higher than about 14%, the resulting hyaluronic acid derivative has extremely high permeability through a filter of 0.22 µm pore diameter which is generally used for filter sterilization.

A solution, in which a solute is sufficiently dispersed and dissolved in a solvent, generally passes through a filter without a significant decrease in concentration. In addition to the molecular dispersion and the solubility of the polysaccharide derivative, there are other factors that affect the filter permeability. For example, when the organic compound to be bound to the polysaccharide has high hydrophobicity, non-specific adsorption of the hydrophobic portion to the filter material may lower the filter permeability with an increase in degree of substitution of the organic compound.

The production method of the present invention can produce the polysaccharide derivative while maintaining the high hydrophilicity over the whole production process. Namely, the hyaluronic acid derivative to be produced by the production method of the present invention maintains the original higher-order structure of hyaluronic acid and the higher-order structure-derived characteristics. The production method of the present invention yields a hyaluronic acid derivative or another polysaccharide derivative that has not only the original characteristics of a polysaccharide having a carboxyl group but also the characteristics of an organic compound to be linked to the carboxyl group. When a physiologically active substance, a medicinal substance, or the physiologically active substance or the medicinal substance that is linked with a spacer compound, such as a lower alcohol or amino acid, in a decomposable manner under physiological conditions is used as an organic compound having a functional group for synthesis of the polysaccharide derivative, the resulting polysaccharide derivative is used as a excellent sustained release drug without losing the characteristics of the polysaccharide.

For example, for producing a polysaccharide derivative that is applicable to treat inflammation and pain accompanied by arthropathy, a covalently linked substance of an NSAID as an anti-inflammatory drug and an aminoalkyl alcohol (spacer compound) such as aminoethanol or aminopropanol by ester bond of the carboxyl group of the NSAID with the hydroxyl group of the aminoalkyl alcohol is selected as the organic compound having the functional group capable of condensing with a carboxyl group. On the other hand, hyaluronic acid, which is generally applied for treatment of arthropathy, is selected as the polysaccharide having a carboxyl group. Then, the amino group of the amino alkyl alcohol is condensed with the carboxyl group of hyaluronic acid in the production method of the present invention. The obtained hyaluronic acid derivative keeps high water solubility and is readily applicable to an effective drug for injection or another local application. The hyaluronic acid derivative has ester bond that is decomposed in a living body and accordingly attains the sustained release property of the NSAID.

EXAMPLES

The present invention is described below in detail based on examples. However, the scope of the present invention is not restricted to these examples.

In all examples, sodium hyaluronate was purchased from Seikagaku Corporation, and 4-(4,6-dimethoxy-1,3,5-triazin-2-yl)-4-methylmorpholinium chloride (DMT-MM) was purchased from Wako Pure Chemical Industries, Ltd. (Lot. EWRO0514). Aminoethanol-diclofenac hydrochloride was prepared by the procedure described in Reference Example 5 and Example 38 of WO2005/066214. Aminopropanol-cinnamate hydrochloride (3-aminopropyl cinnamate hydrochloride) was prepared by the procedure described in Example 1 of Japanese Patent No. 3343181 and Example 1 of U.S. Pat. No. 6,025,444.

<Measurement>
Measurement of Degree of Substitution

In the experiments below, degree of substitution was measured by spectrophotometry, unless otherwise specified. Specifically, the quantity of hyaluronic acid in each sample solution was determined by the carbazole-sulfuric acid reaction, and the quantity of each compound introduced was determined by spectrophotometry, and then the degree of substitution was calculated from the two quantitative values.

As for the measurement of aminoethanol-diclofenac group, each sample solution was dissolved in distilled water and the quantity of diclofenac was determined from the diclofenac based absorbance at about 280 nm by spectrophotometry.

As for the measurement of aminopropanol-cinnamate group, each sample solution was dissolved in 0.1 mol/L aqueous sodium hydroxide solution and the quantity of cinnamate group was determined from the cinnamate group-based absorbance at about 269 nm by spectrophotometry.

Reference Example 1

Synthesis of aminoethanol-diclofenac-introduced sodium hyaluronate

In 22.5 mL water/22.5 mL dioxane, 200 mg of sodium hyaluronate having the weight average molecular weight of 800,000 was dissolved, and then 0.450 mL of 1 mol/L aqueous N-hydroxysuccinimide (HOSu) solution, 0.450 mL of 0.5 mol/L aqueous water-soluble carbodiimide hydrochloride (WSCI.HCl) solution, and 2.25 mL of 0.1 mol/L amino-ethanol-diclofenac hydrochloride solution (water: dioxane=1:1) were sequentially added and stirred overnight. The reaction solution was divided into two equal portions, and one of the two portions was used for Reference Example 1 and the other portion was used for Reference Example 2. After addition and dissolution of 0.5 g of sodium chloride into the one portion of the reaction solution, the mixture was precipitated by adding 100 mL of ethanol. The precipitate was sequentially washed with 85% ethanol twice, with ethanol twice, and with diethyl ether once and was dried overnight under reduced pressure at room temperature to give 113.3 mg portion of a white solid.

Reference Example 2

Synthesis of aminoethanol-diclofenac-introduced sodium hyaluronate

To the other portion of the reaction solution prepared in Reference Example 1, 1.5 mL of 5% aqueous sodium hydrogen carbonate solution was added, followed by stirring for 3.5 hours. After neutralizing the reaction solution by adding 50% acetic acid, 0.5 g of sodium chloride was added. The mixture was precipitated by adding 100 mL of ethanol. The precipitate was sequentially washed with 85% ethanol twice, with ethanol twice, and with diethyl ether once and was dried overnight under reduced pressure at room temperature to give 111.5 mg portion of a white solid. The degree of substitution was 20.6%.

Reference Example 3

Synthesis of aminoethanol-diclofenac-introduced sodium hyaluronate

In 15.7 mL of water/15.7 mL of dioxane, 133 mg of sodium hyaluronate having the weight average molecular weight of 800,000 was dissolved, and then 0.267 mL of 1 mol/L aqueous HOSu solution, 0.267 mL of 0.5 mol/L aqueous WSCI.HCl solution, and 0.933 mL of 0.143 mol/L aminoethanol-diclofenac hydrochloride solution (water:dioxane=1:1) were sequentially added, and stirred overnight. To the reaction solution, 4 mL of 5% aqueous sodium hydrogen carbonate solution was added, and stirred for 3 hours. After neutralizing the reaction solution by adding 50% acetic acid, 0.67 g of sodium chloride was added. The mixture was precipitated by adding 133 mL of ethanol. The precipitate was sequentially washed with 85% ethanol twice, with ethanol twice, and with diethyl ether once and was dried overnight under reduced pressure at room temperature to give 124.0 mg portion of a white solid. The degree of substitution was 14.3%.

Reference Example 4

Synthesis of aminoethanol-diclofenac-introduced sodium hyaluronate

In Reference Example 4, 124.0 mg of a white solid substance was obtained as the resulting product by the same procedure as that of Reference Example 3 except that the stirring time was changed from 3 hours to 1 hour after addition of the 5% aqueous sodium hydrogen carbonate to the reaction solution.

Example 1

Synthesis of aminoethanol-diclofenac-introduced sodium hyaluronate

In 10 mL water/10 mL of ethanol, 100 mg of sodium hyaluronate having a weight average molecular weight of 800,000 was dissolved and then 0.556 mL of 0.0676 mol/L aminoethanol-diclofenac hydrochloride solution (water:ethanol=1:1) and 0.800 mL of 16.8 mg/mL DMT-MM solution (water:ethanol=1:1) were sequentially added, and stirred overnight. After addition of 0.5 g of sodium chloride into the reaction solution, the mixture was precipitated by adding 100 mL of ethanol. The precipitate was sequentially washed with 85% ethanol twice, with ethanol twice, and with diethyl ether once and was dried overnight under reduced pressure at room temperature to give 87.6 mg portion of a white solid. The degree of substitution was 13.8%.

Example 2

Synthesis of aminoethanol-diclofenac-introduced sodium hyaluronate

In Example 2, 103.5 mg of a white solid substance was obtained as the resulting product by the same procedure as that of Working Example 1 except that 0.800 mL of 0.05 mol/L aminoethanol-diclofenac hydrochloride solution (water:ethanol=1:1) and 0.800 mL of 22.4 mg/mL DMT-MM solution (water:ethanol=1:1) was added to the hyaluronate solution. The degree of substitution was 19.7%.

Example 3

Synthesis of aminoethanol-diclofenac-introduced sodium hyaluronate

In 30 mL water/30 mL ethanol, 300 mg of sodium hyaluronate having a weight average molecular weight of 80,000 was dissolved, and then 1.50 mL of 0.0805 mol/L aminoethanol-diclofenac hydrochloride solution (water:ethanol=1:1) and 1.50 mL of 35.9 mg/mL DMT-MM solution (water:ethanol=1:1) were sequentially added, and stirred overnight. To the reaction solution, 4.5 mL of 5% aqueous sodium hydrogen carbonate solution was added and stirred for 3.5 hours. After neutralizing the reaction solution by adding 50% acetic acid, the mixture was precipitated by adding 300 mL of ethanol. The precipitate was sequentially washed with 85% ethanol twice, with ethanol twice, and with diethyl ether twice and was dried overnight under reduced pressure at room temperature to give 294.8 mg portion of a white solid. The degree of substitution was 18.7%.

Example 4

Synthesis of aminopropanol-cinnamate-introduced sodium hyaluronate

In 20 mL of water/20 mL ethanol, 200 mg of sodium hyaluronate having the weight average molecular weight of 80,000 was dissolved, and then 1.0 mL of 0.101 mol/L aminopropanol-cinnamate hydrochloride solution (water:ethanol=1:1) and 1.0 mL of 45.0 mg/mL DMT-MM solution (water:ethanol=1:1) were sequentially added, and stirred overnight. The mixture was precipitated by adding 200 mL of ethanol. The precipitate was sequentially washed with 85% ethanol twice, with ethanol twice, and with diethyl ether once and was dried overnight under reduced pressure at room temperature to give 197.7 mg portion of a white solid. The degree of substitution was 16.3%.

Example 5

Synthesis of aminopropanol-cinnamate-introduced sodium hyaluronate

In 10 mL water/10 mL ethanol, 100 mg of sodium hyaluronate having a weight average molecular weight of 800,000 was dissolved, and then 0.286 mL of 0.132 mol/L aminopropanol-cinnamate hydrochloride solution (water:ethanol=1:1) and 0.286 mL of 59.0 mg/mL DMT-MM solution (water:ethanol=1:1) were sequentially added, and stirred overnight. To the reaction solution, 1.5 mL of 5% aqueous sodium hydrogen carbonate solution was added, and stirred for 2 hours. After neutralizing the reaction solution by adding 50% acetic acid, the mixture was precipitated by adding 100 mL of ethanol. The precipitate was sequentially washed with 85% ethanol twice, with ethanol twice, and with diethyl ether once and was dried overnight under reduced pressure at room temperature to give 90.4 mg portion of a white solid. The degree of substitution was 12.3%.

Example 6

Synthesis of n-amylamine-introduced sodium hyaluronate

In 40 mL water/40 mL ethanol, 400 mg of sodium hyaluronate having a weight average molecular weight of 80,000 was dissolved, and then 1.8 g of 0.167 mmol/g n-amylamine hydrochloride (manufactured by Wako Pure Chemical Industries, Ltd.) solution (water:ethanol=1:1) and 3.0 mL of 45.0 mg/mL DMT-MM solution (water:ethanol=1:1) were sequentially added, and stirred overnight. The reaction solution was divided into two equal portions, and one of the two portions was used for Example 6 and the other portion was used for Example 7. After addition and dissolution of 1 g of sodium chloride into the one portion of the reaction solution, the mixture was precipitated by adding 200 mL of ethanol. The precipitate was sequentially washed with 85% ethanol ten times, with ethanol twice, and with diethyl ether once and was dried overnight under reduced pressure at room temperature to give 188.7 mg portion of a white solid.

Example 7

Synthesis of n-amylamine-introduced sodium hyaluronate

To the other portion of the reaction solution prepared in Example 6, 3.0 mL of 5% aqueous sodium hydrogen carbonate solution was added, and stirred for 3 hours. After neutralizing the reaction solution by adding 50% acetic acid and addition and dissolution of 1 g of sodium chloride into the reaction solution, the mixture was precipitated by adding 200 mL of ethanol. The precipitate was sequentially washed with 85% ethanol ten times, with ethanol twice, and with diethyl ether once and was dried overnight under reduced pressure at room temperature to give 185.5 mg portion of a white solid. The degree of substitution measured by $^1$H-NMR ($D_2O$) was 22%.

Test Example 1

The aminoethanol-diclofenac-introduced sodium hyaluronate prepared in Examples 2 and 3, the aminopropanol-cinnamate introduced sodium hyaluronate prepared in Examples 4 and 5, and the n-amylamine-introduced sodium hyaluronate prepared in Examples 6 and 7 were respectively added with distilled water so that the concentration of each of the hyaluronic acid derivatives was 1.0% in the sealed bottles, followed by shaking at 220 rpm over night at room temperature. The aminoethanol-diclofenac-introduced sodium hyaluronate prepared in Reference Examples 1 and 2 were tested by the same procedure. The derivatives of Examples 2, 3, 4, 5, 6, and 7 and the derivative of Reference Example 2 were all homogeneously dissolved in distilled water and yielded clear and viscous aqueous solutions. The aminoethanol-diclofenac-introduced sodium hyaluronate of Reference Example 1 was not dissolved in distilled water but yielded a white suspension.

Test Example 2

The aminoethanol-diclofenac-introduced sodium hyaluronate prepared in Example 1 and Reference Examples 3 and 4 were respectively mixed with distilled water so that the concentration of each of the derivatives was 1.0% (w/v) in the sealed bottles, followed by shaking at 220 rpm over night at room temperature. Each of the aqueous solutions (test solutions) was injected into a rear portion of a syringe (1 mL in volume: manufactured by TERUMO Corporation) equipped with a porous filter (Millex-GV of 0.22 µm pore diameter: manufactured by Millipore Corporation) and was pressed out with a piston at room temperature to pass through the porous filter.

The diclofenac-based absorbance (peak top) at about 280 nm was measured for each of the test solutions before, and after the filter passage of at least 0.5 mL. The filter passage coefficient of each test solution was expressed by a concentration of the diclofenac content in the test solution before and after the filter passage that was calculated from the change in measured absorbance.

The filter passage coefficients of the aqueous solution of Example 1 and the aqueous solution of Reference Example 3 were respective 95.3% and 96.9%. Namely, both the aqueous solutions of Example 1 and Reference Example 3 almost fully passed through the porous filter. The filter passage coefficient of the aqueous solution of Reference Example 4 was only 11.0%. This low filter passage coefficient may be ascribed to the shorter stirring time and the resulting insufficient treatment after addition of the 5% aqueous sodium hydrogen carbonate solution in Reference Example 4, compared with Reference Example 3.

The aminopropanol-cinnamate-introduced sodium hyaluronate prepared in Example 5 was tested by the same procedure. The filter passage coefficient of this aqueous solution was 81.6%.

INDUSTRIAL APPLICABILITY

The production method of the present invention enables efficient and easy production of a derivative of a polysaccharide having a carboxylic group, such as sodium hyaluronate, and is effectively applied for industrial scale production of such polysaccharide derivatives. The polysaccharide derivatives obtained by the production method of the present invention have significantly higher solubility in aqueous solvents, as compared with polysaccharide derivatives obtained by the prior art production methods.

What is claimed is:

1. A method of producing a polysaccharide derivative comprising a polysaccharide having a carboxyl group bound to an organic compound having a functional group capable of condensing with the carboxyl group, which comprises reacting the polysaccharide with the organic compound by the use of a condensing agent shown by the general formula (1):

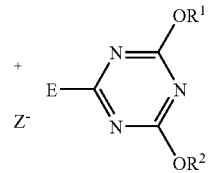

wherein $R^1$ and $R^2$ independently represent a substituent selected among alkyl groups of 1 to 4 carbon atoms and aryl groups of 6 to 8 carbon atoms; $Z^-$ represents a counter anion; and $E^+$ represents the following group:

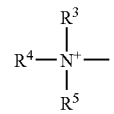

wherein $R^3$, $R^4$, and $R^5$ independently represent an organic group having at least one carbon atom directly bound to the quaternary nitrogen atom and any two or all of $R^3$, $R^4$, and $R^5$ may link together to form a cyclic structure, wherein the polysaccharide having a carboxyl group is a hyaluronic acid having a weight average molecular weight of 100,000 to 5,000,000, and wherein the rate of the introduced organic compound per disaccharide unit of the hyaluronic acid is not less than 5%.

2. The method according to claim 1, wherein the organic compound is an organic compound having a hydroxyl group or an amino group, and wherein the polysaccharide and the organic compound are bound by an ester bond or amide bond.

3. The method according to claim 2, wherein the organic compound is a compound having at least one amino group, and wherein the polysaccharide and the organic compound are bound by an amide bond.

4. The method according to claim 1, wherein in the general formula (1), $R^1$ and $R^2$ are independently selected from the group of a methyl group, an ethyl group, and a phenyl group, $E^+$ is an N-methylmorpholinium group, and $Z^-$ is a chlorine anion, a perchlorate anion, or a tetrafluoroborate anion.

5. The method according to claim 4, wherein the compound shown by the general formula (1) is 4-(4,6-dimethoxy-1,3,5-triazin-2-yl)-4-methylmorpholinium chloride.

6. The method according to claim 2, wherein the organic compound is selected from the group consisting of linear alkylamines, amino acids, aminoalkylalcohols and their derivatives.

7. The method according to claim 2, wherein the organic compound is selected from the group consisting of cytokines, hormones, growth factors, enzymes, and medicinal substances.

8. The method according to claim 7, wherein the medicinal substance is nonsteroidal anti-inflammatory drug (NSAID) or disease-modifying antirheumatic drug.

9. The method according to claim 1, wherein the organic compound is a compound obtained by covalently linking a cytokine, hormone, growth factor, enzyme, medicinal substance, or photoreactive compound to a spacer substance having two functional groups, wherein the spacer substance has a functional group capable of condensing with a carboxyl group of the polysaccharide and a functional group capable of condensing with a functional group of the cytokine, hormone, growth factor, enzyme, medicinal substance, or photoreactive compound.

10. The method according to claim 9, wherein the organic compound is a compound obtained by covalently linking cinnamic acid, cinnamate derivative or NSAID to the spacer substance.

11. The method according to 10, wherein the spacer substance is selected from a group consisting of aminoalkylalcohols having 2 to 12 carbon atoms, alkylenediamines having 2 to 18 carbon atoms, and amino acids.

12. The method according to claim 11, wherein the organic compound is a compound obtained by covalently linking cinnamic acid, cinnamate derivative or NSAID to an aminoalkylalcohol having 2 to 12 carbon atoms by ester bond of the carboxyl group of the cinnamic acid, cinnamate derivative or NSAID with the hydroxyl group of the aminoalkyl alcohol.

13. The method according to claim 12, wherein the organic compound is a compound obtained by covalently linking NSAID to an aminoethanol by ester bond of the carboxyl group of the NSAID with the hydroxyl group of the aminoethanol.

14. The method according to claim 12, wherein the organic compound is a compound obtained by covalently linking cinnamic acid, or cinnamate derivative to an aminopropanol by ester bond of the carboxyl group of the cinnamic acid, or cinnamate derivative with the hydroxyl group of the aminopropanol.

15. The method according to claim 6, wherein the organic compound is linear alkylamine, or its derivative.

16. A method of producing a hyaluronic acid derivative which is highly soluble in an aqueous solvent, which comprises reacting a hyaluronic acid having a weight average molecular weight of 100,000 to 5,000,000 with an organic compound having a functional group capable of condensing with carboxyl group by the use of 4-(4,6-dimethoxy -1,3,5-triazin-2-yl)-4-methylmorpholinium chloride as a condensing agent,
wherein the rate of the introduced organic compound per disaccharide unit of the hyaluronic acid is not less than 5%.

17. The method according to claim 5, wherein the organic compound is selected from the group consisting of linear alkylamines, amino acids, aminoalkylalcohols and their derivatives.

18. The method according to claim 5, wherein the organic compound is selected from the group consisting of cytokines, hormones, growth factors, enzymes, and medicinal substances.

19. The method according to claim 18, wherein the medicinal substance is nonsteroidal anti-inflammatory drug (NSAID) or disease-modifying antirheumatic drug.

20. The method according to claim 5, wherein the organic compound is a compound obtained by covalently linking a cytokine, hormone, growth factor, enzyme, medicinal substance, or photoreactive compound to a spacer substance having two functional groups,
wherein the spacer substance has a functional group capable of condensing with a carboxyl group of the polysaccharide and a functional group capable of condensing with a functional group of the cytokine, hormone, growth factor, enzyme, medicinal substance, or photoreactive compound.

* * * * *

UNITED STATES PATENT AND TRADEMARK OFFICE
CERTIFICATE OF CORRECTION

PATENT NO. : 8,557,986 B2  
APPLICATION NO. : 12/299091  
DATED : October 15, 2013  
INVENTOR(S) : Yasuda It is certified that error appears in the above-identified patent and that said Letters Patent is hereby corrected as shown below:

Title Page 1 (item 57, Abstract) at line 6, Change "an an" to --an--.

In the Specification

In column 5 at line 62, Change "D-glucoronic" to --D-glucuronic--.

In column 7 at lines 57-65, Change

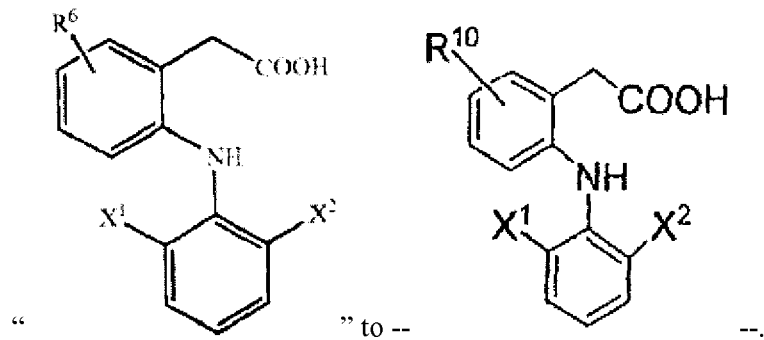

In column 10 at line 54, Change "4-dixoane" to --4-dioxane--.

In the Claims

In column 19 at line 8, In Claim 11, change "to" to --to claim--.

Signed and Sealed this  
Tenth Day of June, 2014

Michelle K. Lee  
*Deputy Director of the United States Patent and Trademark Office*

UNITED STATES PATENT AND TRADEMARK OFFICE
CERTIFICATE OF CORRECTION

PATENT NO. : 8,557,986 B2  Page 1 of 1
APPLICATION NO. : 12/299091
DATED : October 15, 2013
INVENTOR(S) : Yousuke Yasuda It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 766 days.

Signed and Sealed this

Fifteenth Day of September, 2015

Michelle K. Lee
*Director of the United States Patent and Trademark Office*